(12) United States Patent
Peterson, Jr. et al.

(10) Patent No.: US 6,959,602 B2
(45) Date of Patent: Nov. 1, 2005

(54) ULTRASONIC DETECTION OF POROUS MEDIUM CHARACTERISTICS

(75) Inventors: Michael L. Peterson, Jr., Orono, ME (US); Anthony DiLeo, Westford, MA (US); Zong Mu Wang, Old Town, ME (US); Alan Greenberg, Boulder, CO (US)

(73) Assignee: Millipore Corporation, Billerica, MA (US)

(*) Notice: Subject to any disclaimer, the term of this patent is extended or adjusted under 35 U.S.C. 154(b) by 0 days.

(21) Appl. No.: 10/388,386

(22) Filed: Mar. 12, 2003

(65) Prior Publication Data

US 2003/0217599 A1 Nov. 27, 2003

Related U.S. Application Data

(60) Provisional application No. 60/366,067, filed on Mar. 19, 2002.

(51) Int. Cl.[7] .............................................. G01N 29/00
(52) U.S. Cl. ........................................ 73/602; 73/597
(58) Field of Search ........................ 73/602, 597, 598, 73/599, 600, 632, 628

(56) References Cited

U.S. PATENT DOCUMENTS

| | | | |
|---|---|---|---|
| 3,645,129 A | 2/1972 | Grant | |
| 4,283,952 A | 8/1981 | Newman | |
| 4,356,422 A | * 10/1982 | van Maanen | ................ 310/322 |
| 4,457,174 A | 7/1984 | Bar-Cohen et al. | |
| 4,674,334 A | 6/1987 | Chimenti et al. | |
| 4,976,150 A | * 12/1990 | Deka | ........................... 73/644 |
| 5,082,366 A | 1/1992 | Tyson, II et al. | |
| 5,091,776 A | 2/1992 | Tyson, II | |
| 5,094,528 A | 3/1992 | Tyson, II et al. | |
| 5,146,209 A | 9/1992 | Beghelli | |
| 5,146,289 A | 9/1992 | Newman | |
| 5,176,034 A | * 1/1993 | Hazony et al. | ................ 73/597 |
| 5,257,088 A | 10/1993 | Tyson, II et al. | |
| 5,307,139 A | 4/1994 | Tyson, II et al. | |
| 5,410,406 A | 4/1995 | Webster | |
| 5,469,742 A | 11/1995 | Lee et al. | |
| 5,481,356 A | 1/1996 | Pouet et al. | |
| 5,637,799 A | * 6/1997 | Heyman et al. | ............... 73/600 |

(Continued)

FOREIGN PATENT DOCUMENTS

| | | |
|---|---|---|
| EP | 0 473 173 A2 | 3/1992 |
| EP | 0 492 559 A2 | 7/1992 |
| EP | 0 554 477 B1 | 8/1996 |
| EP | 1 099 947 A2 | 5/2001 |
| WO | WO 97/39306 | 10/1997 |

OTHER PUBLICATIONS

Berryman, J.G., "Confirmation of Biot's theory", *Appl. Phys. Lett.* 37(4), 382–384, Aug. 15, 1980.

(Continued)

*Primary Examiner*—Hezron Williams
*Assistant Examiner*—Jacques M. Saint-Surin
(74) *Attorney, Agent, or Firm*—Hamillton, Brook, Smith & Reynolds, P.C.

(57) ABSTRACT

Plate waves are used to determine the presence of defects within a porous medium, such as a membrane. An acoustic wave can be propagated through a porous medium to create a plate wave within the medium. The plate wave creates fast compression waves and slow compression waves within the medium that relate to the material and structural properties of the medium. The fast compression wave provides information about the total porosity of a medium. While the slow compression wave provides information about the presence of defects in the medium or the types of materials that form the medium.

29 Claims, 13 Drawing Sheets

U.S. PATENT DOCUMENTS

| | | | | |
|---|---|---|---|---|
| 5,668,303 A | * | 9/1997 | Giesler et al. | 73/24.06 |
| 5,956,143 A | | 9/1999 | Kotidis | |
| 5,987,991 A | * | 11/1999 | Trantow et al. | 73/624 |
| 6,040,900 A | | 3/2000 | Chen | |
| 6,092,421 A | * | 7/2000 | Bar-Cohen et al. | 73/624 |
| 6,182,510 B1 | * | 2/2001 | Stanke et al. | 73/597 |
| 6,247,367 B1 | * | 6/2001 | Bar-Cohen et al. | 73/628 |
| 6,257,048 B1 | | 7/2001 | Hietala et al. | |
| 6,606,909 B2 | * | 8/2003 | Dubois et al. | 73/600 |
| 6,691,577 B1 | * | 2/2004 | Toda | 73/602 |

OTHER PUBLICATIONS

Biot, M.A., "Theory of Propagation of Elastic Waves in a Fluid–Saturated Porous Solid. I. Low–Frequency Range", *The Journal of the Acoustical Society of America*, vol. 28, No. 2, 168–178, Mar., 1956.

Biot, M.A., "Theory of Propagation of Elastic Waves in a Fluid–Saturated Porous Solid. II. Higher–Frequency Range", *The Journal of the Acoustical Society of America*, vol. 28, No. 2, 179–191, Mar., 1956.

Biot, M.A., "Generalized Theory of Acoustic Propagation in Porous Dissipative Media*", *The Journal of the Acoustical Society of America*, vol. 34, No. 9, 1254–1264, Sep. 1962.

Plona, T.J., "Observation of a second bulk compressional wave in a porous medium at ultrasonic frequencies", *Appl. Phys. Lett.* 36(4), 259–261, Feb. 15, 1980.

Jiang, L.J., et al., (XP 008023914), "Non–Destructive Tests of Latex Membrane with Electronic Speckle Pattern Interferometry", *Final Program & Book of Abstracts, 1999 ASME Mechanics & Materials Conference*, Jul. 27–30, 1999.

Johnson, M.A., et al., (XP 000658827), "Antisymmetric nature of the earliest arrivals of ultrasound propogating in copy paper", *J. Acoustical Society of America* 101 (5), May 1997, Pt. 1:2986:2989.

Pouet, B.F., et al., (XP 000473130), "Additive–subtractive phase–modulated electronic speckle interferometry: analysis of fringe visibility", *Applied Optics (Optical Society of America)*, Oct. 1, 1994, vol. 33, No. 28:6609–6616.

Taylor, D.J., et al., (XP 4223471A1), "Technique for characterization of thin film porosity", *Thin Solid Films* 332 (1998) 257–261, *Elsevier Science S.A.*.

Wang, L–S., et al., (XP 000597470), " Additive–subtractive speckle interferometry: extraction of phase data in noisy environments", *Optical Engineering*, Mar. 1996, vol. 35, No. 3:794–801.

Yang, L.X., et al., (XP 004040393), "Precision measurement and nondestructive testing by means of digital phase shifting speckle pattern and speckle pattern sharing interferometry", *Measurement*, (1995), vol. 16:149–160.

Yoseph Bar–Cohen et al., *Characterization of Defects in Composite Material Using Rapidly Acquired Leaky Lamb Wave Dispersion Data*, [online] NDT.NET vol. 3 No. 9 (Sep. 1998) [retrieved on Jul. 1, 2003] Retrieved from the Internet <URL:http://www.ndt.net/article/ecndt98/aero/013/013.htm>.

* cited by examiner

ULTRASONIC DETECTION OF POROUS MEDIUM CHARACTERISTICS

RELATED APPLICATION

This application claims the benefit of U.S. Provisional Application No. 60/366,067 filed Mar. 19, 2002. The entire teachings of the above application are incorporated herein by reference.

BACKGROUND OF THE INVENTION

Quality assurance is an important aspect of membrane module fabrication. A continuing need exists for improved nondestructive test techniques for the characterization of membranes during the fabrication process, as well as during operation of the membranes.

Ultrasonic testing has been previously used as a nondestructive test in the characterization of membrane properties. For example, longitudinal waves transmitted through a membrane from an ultrasonic source have been used as a nondestructive method of membrane testing. Behavior of the longitudinal waves within the membrane describe the physics of membrane formation, compaction, and fouling in terms of sound wave propagation within the membrane.

The reflection and transmission of elastic waves in porous media has received considerable attention because of the importance of the problem in earthquake engineering, geophysics, and soil engineering. More recently, interest has been generated in the area of applications for ultrasonic testing of porous materials such as foams. The problem has also been explored because of interest in the physics of the phenomena at a fundamental level and the possible impact on measurements in other higher density materials.

Material property characterization in elastic plates and the measurement of properties of layered plates using guided elastic waves are well-established techniques in both geophysics and non-destructive evaluation of composite materials. However, only some of these techniques are well suited for applications in materials that are as thin as microporous membranes. In addition, the issues associated with obtaining required material property values for even relatively thick porous materials present a significant challenge.

SUMMARY OF THE INVENTION

Detection of defects in microporous films, such as membranes, can be performed by characterizing the propagation of plate waves in a porous film and evaluating the scattering from a hole in the porous film.

One embodiment of the invention relates to a method for determining a porous film characteristic. This method involves the steps of acoustically coupling at least one transducer to a porous film, producing a plate wave in the porous film by propagating an acoustic wave within the porous film, and obtaining a representative signal for the porous film. The representative signal for the porous film can be compared with a reference signal from a reference porous film. A porous film characteristic is then determined. The porous film can be a membrane.

The at least one transducer can be acoustically coupled to the porous film at an angle relative to the surface of the porous film or along an axis parallel to the surface of the porous film. The at least one transducer can be impedance matched to the porous film material, such as by attaching an epoxy resin coupling device having a glass particle filler between the at least one transducer and the porous film. At least one surface of the porous film can be in contact with a liquid medium or a gaseous medium.

The step of determining the characteristic of the porous film can include determining the material properties of the porous film, determining the total porosity of the porous film, or determining the presence of a defect in the porous film. The defect can be less than about one wavelength in size, for example.

The method for determining a porous film characteristic can also include the step of distinguishing a fast compression wave and a slow compression wave in the porous film. Fast compression waves are more sensitive to the total porosity of a porous film and can be used to determine the porosity in a porous film or pore fouling. Slow compression are less sensitive to porous film porosity and can be used to indicate the presence of a defect in a porous film, the type of material that forms a porous film, or porous film surface fouling, for example. The time difference between the slow compression wave and the fast compression wave can be used to determine the total porosity of the porous film and/or the presence of defects in the porous film.

Another embodiment of the invention relates to a method for determining a material characteristic of a porous film. This method includes the steps of acoustically coupling at least one transducer to a porous film, producing a plate wave in the porous film by propagating a sound wave within the porous film, distinguishing a slow compression wave in the porous film, and analyzing the slow compression wave to determine a material characteristic of the porous film.

The material characteristic can include at least one defect within the porous film, the type of material that forms the porous film, or the presence of porous film fouling. Analysis of the slow compression wave can be performed by comparing the slow compression wave with a reference slow compression wave.

Another embodiment of the invention relates to a method for determining total porosity in a porous film. This method includes the steps of acoustically coupling at least one transducer to a porous film, producing a plate wave in the porous film by propagating a sound wave within the porous film, distinguishing a fast compression wave in the porous film, and analyzing the fast compression wave to determine the total porosity of the porous film.

The analysis of the fast compression wave can be performed by comparing the fast compression wave with a reference fast compression wave.

In another embodiment, a porous film characteristic of a porous film in a filter device is determined. At least one transducer is acoustically coupled to the porous film. A plate wave in the porous film is produced by propagating an acoustic wave within the porous film. A representative signal is obtained for the porous film. The representative signal for the porous film can be compared with a reference signal from a reference porous film. The porous film characteristic is then determined. A second transducer can be acoustically coupled normal to a surface of the porous film for determining the pore size of the porous film.

If the polymer blend of a membrane differs from pore size to pore size, certain embodiments of the invention can determine the membrane pore size, as well as defects in the membrane. When the polymer blend does not differ, the membrane pore size can be determined by generating a second acoustic wave that is normal to a first acoustic wave generated in the membrane.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

A membrane or a filter device containing a membrane can be nondestructively tested using ultrasonic methods of generating a sound wave in the membrane using an ultrasonic transmitter. The membrane acts as a wave guide for the sound wave, carrying the sound wave along the length of the membrane. The signal produced by the propagation of the wave in the membrane is a "fingerprint" of the particular membrane being tested. This signal provides information relating to the homogeneity of the material forming the membrane along with other information. The presence of a defect in the membrane changes the fingerprint of the membrane. Therefore, comparison of the fingerprint of a known defect-free membrane with a test membrane provides information about the homogeneity of the test membrane. In the illustrated embodiments, the ultrasonic transmitter is a piezoelectric device. Alternatively, laser generation and detection can be used in certain applications.

While different types of waves can be produced in a membrane, plate waves present advantages when used to detect membrane inhomogeneity or the presence of defects because membranes are manufactured as porous structures having a particular thickness. Plate waves can be used to evaluate the size of defects in the membrane and the properties of the membrane material, including porosity. A plate wave can be created in a material having a top free boundary and a bottom free boundary, in contrast to a wave traveling in an unbounded material. Because membranes have a relatively small thickness, a top surface of a membrane acts as a top free boundary and a bottom surface of the membrane acts as a bottom free boundary.

Figure 1:
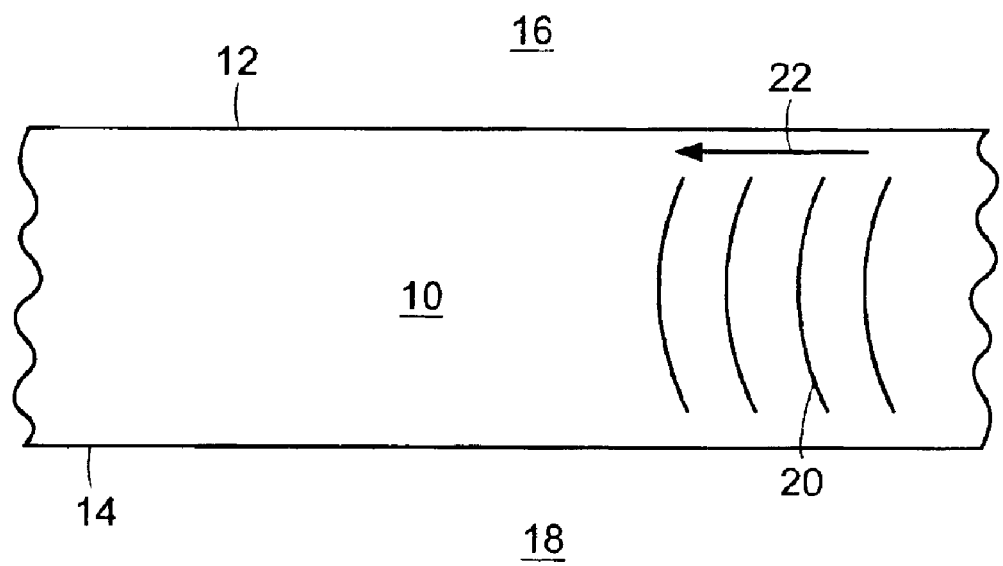
FIG. 1 illustrates a plate wave propagating in a membrane.

FIG. 1 illustrates a membrane 10, or more generally a porous film, having a first or top free boundary 12 and a second or bottom free boundary 14. The first free boundary 12 can abut a first vacuum 16 while the second free boundary 14 can abut a second vacuum 18. Alternatively, either or both boundaries can abut a different media. The presence of the boundaries 12, 14 allows an elastic wave or acoustic wave 20 to propagate along a propagation path 22 in the membrane 10. Elastic waves are periodic, propagating disturbances in a solid medium and can include longitudinal waves that travel along the direction of propagation 22 in the material and that have a velocity that depends upon the elastic moduli of the material. Elastic waves in a solid material can also include transverse or shear waves that travel within the material at a direction perpendicular to the direction of propagation 22. A plate wave is generated through the superposition of shear or longitudinal plane waves in a bounded material. In order to create a plate wave in a material, the free boundary surface of the material should be within approximately ten wavelengths of the elastic disturbance. Therefore, a transducer that generates an elastic disturbance or wave should be in proximity to or in contact with the surface of the material with a wave direction of propagation that is parallel to the free surface in order to create the plate wave.

As is shown in FIG. 1, plate waves are created in a material where the free boundaries 12, 14 of the material abut a non-viscous, fluid medium. It should be noted that plate waves also include Leaky Lamb waves where at least one of the free boundaries of the material abuts a viscous fluid medium, such as water. Other types of waves can propagate in a plate that contacts a solid material.

Plate waves are useful in detecting defects in a membrane because of the potential to inspect relatively large areas in the membrane with a single measurement. A plate wave in a perfectly elastic material attenuates less with distance than a longitudinal wave. Since a membrane is not a perfectly elastic material, attenuation of a plate wave within the membrane as caused by material attenuation still exists, but the attenuation due to beam spreading, or spreading of a wave along the two dimensions of a plane, is reduced. Therefore, the plate wave's reduction in beam spreading and the ability to propagate long distances as a guided wave increases the area that can be inspected with a single ultrasonic transducer or a pair of transducers. For example, a 10-MHz longitudinal wave transmitted from a transducer and directed on the surface of a membrane has a focused area of about 0.2 mm$^2$. The focus area of the transducer can be increased, but requires that the transducer be scanned over the surface of the membrane to inspect the larger area. In contrast, a single 10 millimeter flat transducer can be used to generate a plate wave in a flat-sheet membrane such that the wave propagates over a distance of 300 mm. The area inspected with a plate wave created by a single signal would thus be 3,000 mm². The use of plate waves in membrane inspection, compared to the use of longitudinal waves, increases the area of inspection by a factor of 15,000.

Figure 2:
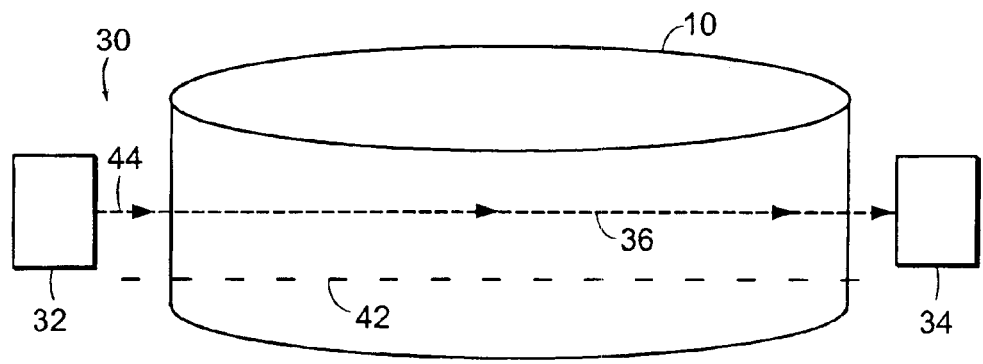
FIG. 2 and FIG. 3 illustrate methods for transmitting a sound wave through a membrane.
Figure 3:
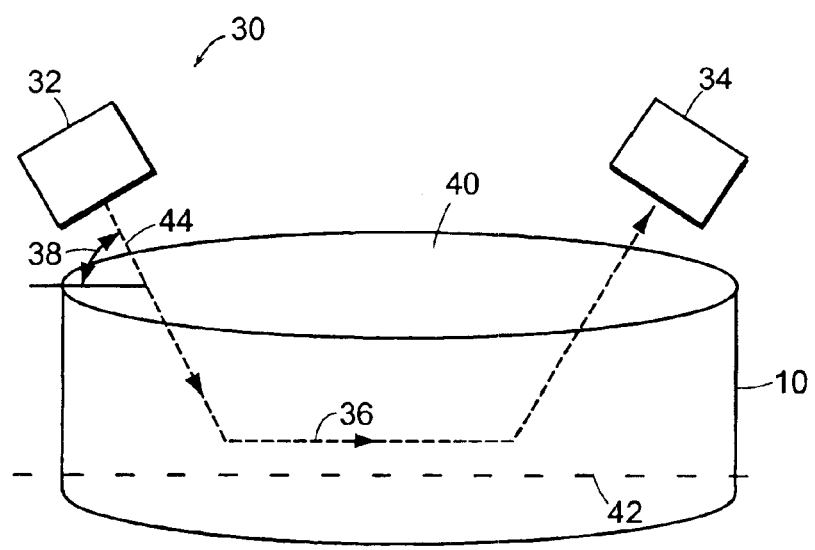

FIGS. 2 and 3 illustrate methods for transmitting a sound wave through a membrane 10. FIG. 2 shows a transducer 30 aligned along a long axis 42 of the membrane 10. The transducer 30 includes a transmitter 32 and a receiver 34. While the transmitter 32 and receiver 34 are shown as separate components of the transducer 30, both the transmitter 32 and receiver 34 can be located within a single transducer component housing and placed against one edge of the membrane 10, or a single piezoelectric transducer can be used as both the transmitter and receiver. To create a plate wave within the membrane 10, the transmitter 32 produces a sound wave 44 which is transmitted through the membrane 10 along wave path 36 and is received by the receiver 34.

FIG. 3 illustrates an alternate configuration of the transducer 30 with respect to the membrane 10. In this configuration, the transducers 30 are placed at an angle 38 relative to a surface 40 of the membrane 10. As is illustrated, the transmitter 32 directs a sound wave 36 at an angle 38 relative to the membrane 10. The sound wave 44 travels through the membrane 10 along wave path 36 and is received by the receiver 34.

The angle 38 formed between the transducer 30 and the surface 40 of the membrane 10 is determined by the constants of the material that comprise the membrane 10. For example, different types or styles of membranes are formed with varying types of materials. The materials that form the different types of membranes influence the refraction angle in the membrane and determine the angle required to create a plate wave in the membranes. When the transducer 30 generates a sound wave 44 at an angle 38 relative to the surface of the membrane 10, the transmission of the signal occurs at a refracted angle which is determined by the propagation of the sound wave 44 in the coupling fluid by the membrane 10. Adjustment of the angle 38 between the transducer 30 and the membrane 10 controls the amount of energy that is coupled into the membrane 10 in the form of a plate wave and can be used to match the energy needed to obtain the required signal from the membrane 10.

Figure 4:
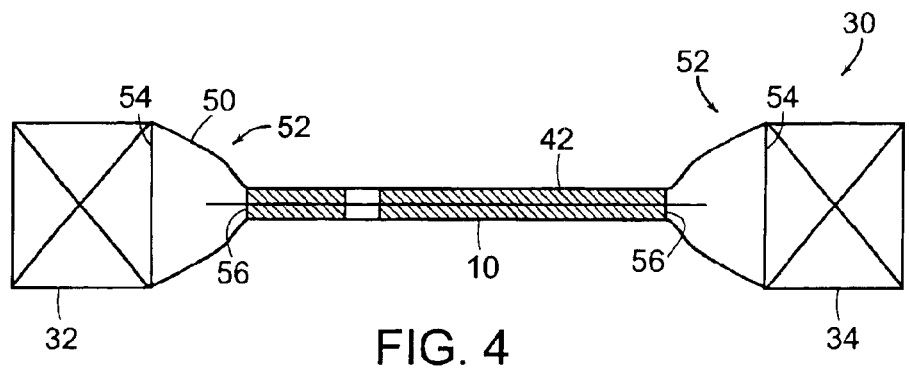
FIG. 4 illustrates the coupling of a membrane to a transducer.

The transducer 30 can also be directly coupled to the membrane 10. A coupling device can be used to provide such a coupling between the membrane 10 and the transducer 30. FIG. 4 illustrates the direct coupling of a membrane 10 to the transmitter 32 and receiver 34 of the transducer 30 by a coupling device 50. The coupling device 50 can be secured to a surface of a membrane 10, such as by clamping the device 50 to the membrane 10, for example, or can be directly cast onto the membrane 10. The coupling device 50 connects the membrane 10 and the transducer 30 along a long axis 42 of the membrane 10. Coupling along the long axis 42 of the membrane 10 can be used in flat sheet or pleated membranes, for example.

The coupling device 50 can include a tapered or curved portion 52 between a transducer coupling surface 54 and a membrane coupling surface 56 of the device 50. The tapered portion 52 decreases the cross-sectional area of the coupling device 50 between the transducer 30 and the membrane 10 such that the membrane coupling surface 56 has a smaller cross-sectional area than the transducer coupling surface 54. The decrease in cross-sectional area of the coupling device 50 between the transducer 30 and the membrane 10 allows the coupling device 50 or lens to focus the sound wave from the transducer 30, having a relatively large diameter, such as a diameter of 25 mm for example, toward the membrane 10 having a relatively small thickness, such as a thickness of 100 micrometers.

For elastic waves, the transmission coefficient of the waves is a function of the product of the wave speed and the density of the material through which the waves are transmitted. This quantity is often referred to as the acoustic impedance, and is analogous to the electrical impedance within an electrical circuit. In order to increase the amplitude of the signal transmitted into the membrane 10, it is necessary to impedance-match the ultrasonic transducer 30 to the membrane material. Impedance matching is important to maintain the amplitude of a signal within the membrane 10 and can be achieved by using appropriate materials in the coupling device 50 between the membrane 10 and the transducer 30.

The high impedance piezo-ceramic used in ultrasonic transducers normally is impedance-matched to a material to be inspected. Contact transducers, for example, are most commonly impedance-matched to metals. The acoustic impedance of steel is approximately 45, whereas the impedance of polytetrafluoroethylene, a material used to form membranes, is 3.0 and the impedance for water is 1.5 (all impedance values times 106 kg/m²s). Thus, for a porous membrane 10, the acoustic impedance match between the membrane 10 and the transducer 30 is relatively poor, since the acoustic impedance of the membrane 10 is lower than the value for the fully dense polymer.

Coupling devices 50 formed of a variety of materials and mounted to the membrane in a variety of geometries can be used. For example, the coupling device 50 can be formed of a polymer, such as epoxy. The epoxy has an impedance value of approximately 4.0 and provides an impedance match between the transducer 30 and membrane 10. The device 50 can also be formed of an epoxy resin having second phase filler or a hollow glass particle filler, such as MICROBALLOONS™ filler. MICROBALLOONS filler is commercially available from W. R. Grace of Columbia, Md. Use of MICROBALLOONS filler with the epoxy lens decreases the base acoustic impedance of the epoxy by up to about seventy percent. The distribution of the MICROBALLOONS filler within the epoxy can be graded to avoid an abrupt transition in acoustic impedance within the coupler 50. This results in an increase in the amount of energy propagated into the membrane 10. By grading the distribution of MICROBALLOONS filler in the coupling device 60, the impedance gradually decreases from the high-impedance piezo-ceramic to the low-impedance membrane.

Figure 5:
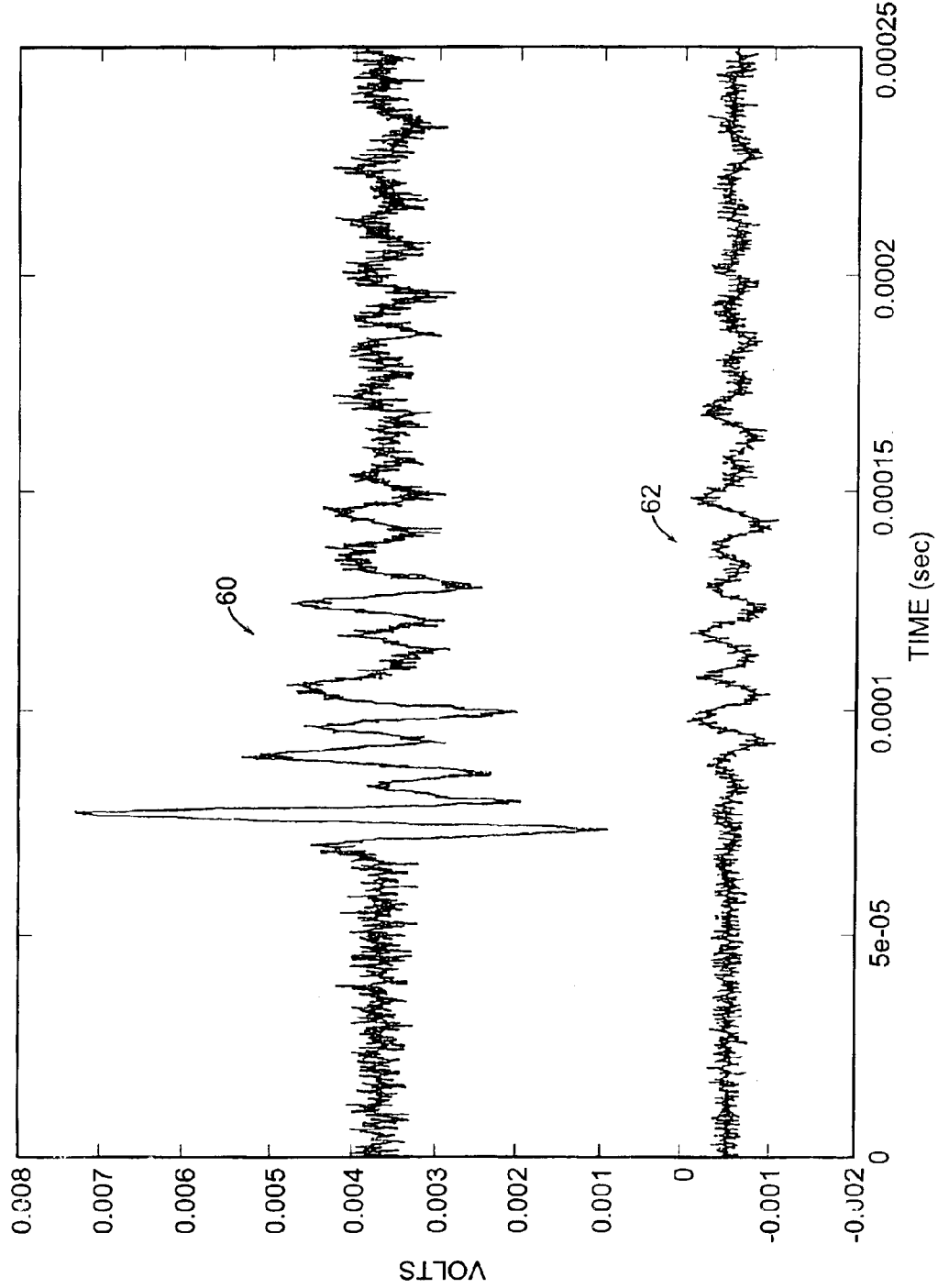
FIG. 5 illustrates a signal produced by a transducer coupled to a membrane.

FIG. 5 shows the effect of the impedance matched coupling device 50 on the amplitude of a plate wave propagated through a membrane 10. The top curve 60 illustrates a signal obtained in a membrane using an epoxy lens having a graded distribution of MICROBALLOONS filler coupling a transmitter to a membrane. The bottom curve 62 illustrates a signal obtained using an unfilled epoxy lens to couple a transducer to a membrane. Both types of coupling devices produce a signal within the membrane. With an unfilled epoxy lens on the transducer, however, the amplitude of the received signal is only slightly above the noise threshold, shown in curve 62. The use of the lens having a graded distribution of MICROBALLOONS filler increases the amplitude of the received signal by approximately a factor of six, shown by curve 60.

The amplitude of the wave put into the membrane is important in determining the presence of defects in the membrane. By using a signal having a relatively large amplitude within the membrane, the presence of defects within the membrane can be more easily detected, compared to the use of a signal having a relatively small amplitude. The technique of impedance matching the transducers to the membrane 10 or placing the transducers at an angle with respect to a surface of the membrane 10 controls the amplitude of the signal delivered to the membrane. While the bandwidth of the signal can be large as shown, a narrow frequency excitation can also be used.

Figure 6:
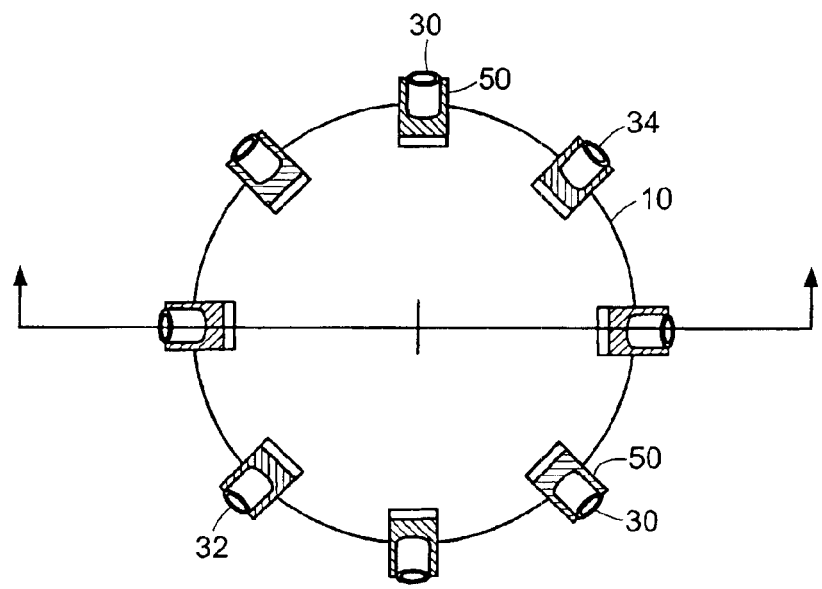
FIG. 6 and FIG. 7 illustrate direct coupling of a transducer to a membrane at an angle relative to the surface of the membrane.
Figure 7:
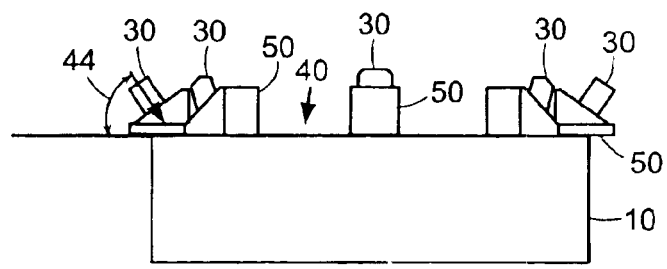

While coupling of the transducers 30 to the membrane 10 along the long axis 42 of the membrane 10 is shown, coupling of the transducers 30 to the membrane 10 at an angle can also be performed. FIGS. 6 and 7 illustrate the direct coupling of transducers 30 at an angle 44 relative to the surface 40 of a membrane 10. The transducers 30 contact the membrane 10 using a coupling device 50 that matches the impedance of the transducers 30 to the impedance of the membrane 10. The coupling device 50 can include a wedge formed from an epoxy material, from an epoxy material having a MICROBALLOONS filler, or from an acrylic material such as plexiglass, for example. Also, as described above, the angle 44 formed between the surface 40 of the membrane 10 and the transducer 30 depends on the material and controls the refraction angle in the material. The angle is determined by the characteristics of the materials that form the membrane 10 as well as the materials that form the coupling device 50.

As is illustrated in FIGS. 6 and 7, the membrane 10 includes transducers 30 located around a perimeter of the membrane 10. A plurality of transducers 30 can be coupled to a membrane 10 in order to inspect a membrane 10 having a relatively large surface area in a single step. The transducers 30 can include a transmitter 32 and a receiver 34 coupled at opposite sides of the membrane 10 at 180° relative to each other. When testing a membrane having a relatively large surface area, the use of a single transducer 30 allows inspection of only a limited surface area of a membrane 10. In order to inspect the entire area of the membrane 10 during an inspection process using a single transducer, either the transducer 30 would have to be positionally adjusted around the circumference of the membrane 10 or the membrane 10 would have to be positionally adjusted relative to the transducer 30. By comparison, the use of multiple transducers 30 positioned around the perimeter of the membrane allows inspection of the entire surface of the membrane 10 without the need to reposition either the membrane 10 or the transducers 30. Alternatively, scanning of the edge can be performed using an air coupled method or laser ultrasonics.

Figure 8:
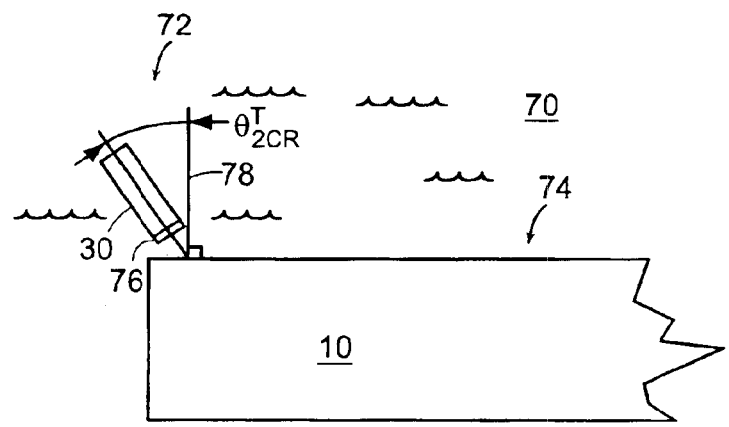
FIG. 8 illustrates the non-contact coupling of a transducer to a membrane.

FIG. 8 illustrates non-contact coupling of a transducer 30 to a membrane 10. At least one surface 74 of the membrane 10 can be in contact with a liquid medium 70, such as water, for example. The transducer 30 is also in contact with the liquid medium 70 and is coupled to the membrane 10 by the liquid medium 70. The transducer 30 includes an impedance matching layer 76 to impedance-match the transducer 30 to the liquid medium 70. During testing, an acoustic or ultrasonic signal is transmitted to the membrane 10 through the liquid medium 70 and generates a plate wave in the membrane. The signal is received by a receiver portion of the transducer 30 and can be used to determine a characteristic of the membrane, such as total porosity of the membrane, pore size distribution, or the presence of a defect in the membrane.

While one surface of the membrane 10 is shown as being in contact with a liquid, alternately, the membrane 10 can be dry and a liquid bead, such as formed by a gel, can be used to couple the membrane 10 to the transducer 30. The liquid bead allows a non-contact coupling of the transducer 30 to the membrane 10.

FIG. 8 also shows the placement of the transducer 30 at an angle 72 relative to a reference or reference line 78 normal to the membrane 10. This second angle 72 or second critical angle depends upon the material characteristics of the coupling fluid 70 and the membrane 10.

Because the properties of microporous membrane materials are not known to have been characterized from the perspective of elastic wave mechanics, a mathematical model has been developed to establish relationships between the material moduli of a membrane and the porosity of a membrane. The effect of fluid filling on wave scattering from a hole or a void in an elastic plate has also been considered. The model considers scattering from a fluid-filled hole that extends through the thickness of a porous, fluid-filled plate, and is related to the scattering caused by a spherical inhomogeneity in a fluid-filled porous medium.

Figure 9:
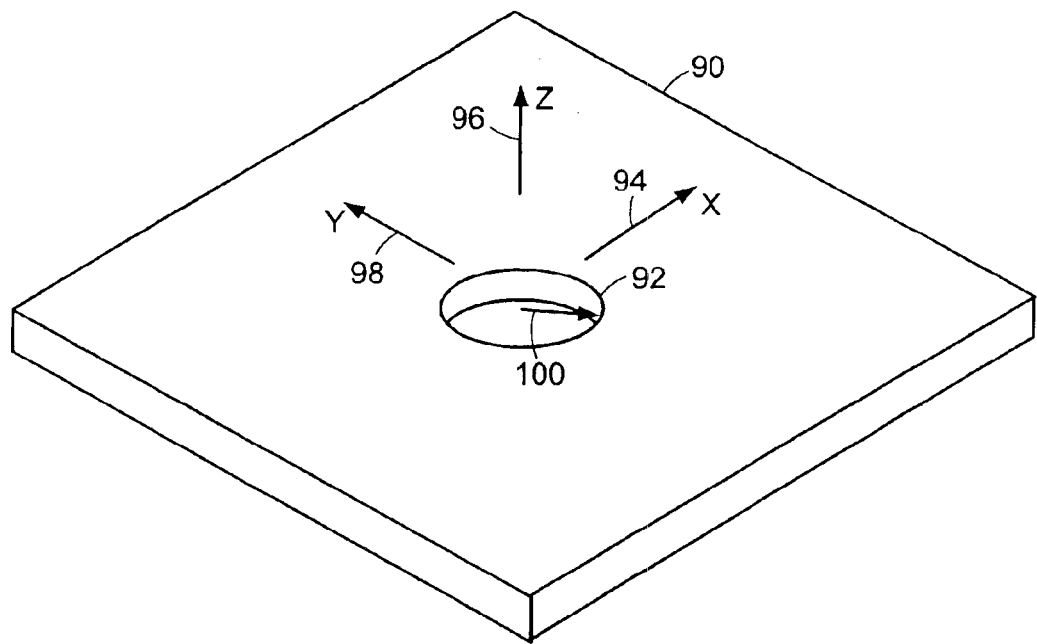
FIG. 9 illustrates a plate having a hole used to model the system.

The configuration of the system to be modeled is illustrated in FIG. 9. The system includes an elastic plate 90 having a defect, represented by an aperture or a void 92 in the plate. The aperture or hole 92 is assumed to completely penetrate the plate 90, or porous membrane, in a region that is in a far field relative to the ultrasonic transducer. The transducer can include a transmitter and a receiver that propagates a symmetric longitudinal plate wave in the membrane 90.

M. A. Biot proposed a simple phenomenological model for acoustic wave propagation in porous, fluid-filled macroscopically homogeneous and isotropic media. This model incorporated the assumption that there exist volumes that are large compared to the pore/grain size length-scale but that are small compared to the wavelength of the elastic wave. Furthermore, each volume element is described by the average displacement of the fluid $U(r,t)$ and of the solid $u(r,t)$. The equations of motion are:

$$\rho_{11}\ddot{u}+\rho_{12}\ddot{U}=P\nabla(\nabla \cdot u)+Q\nabla(\nabla \cdot U)-N\nabla \times \nabla \times u$$

$$\rho_{12}\ddot{u}+\rho_{22}\ddot{U}=Q\nabla(\nabla \cdot u)+R\nabla(\nabla \cdot U)$$

where P, Q and R are generalized elastic coefficients that can be related to the bulk modulus of the material. Because the material is porous, three bulk moduli that are indicated by subscripts are required to define the material. The bulk modulus of the fluid, $K_f$, the bulk modulus of the solid $K_s$ and the bulk modulus of the skeletal frame ("jacketed and drained") $K_b$ define the two constituents and the structure of the material. In addition the shear modulus of both the skeletal frame and of the composite structure, N, is required. These moduli are then defined as:

$$P = \{[(1-\emptyset)\left(1-\frac{K_b}{K_s}\right)K_s + \frac{K_s}{K_f}K_b]/\left(1-\frac{K_b}{K_s}+\frac{K_s}{K_f}\right)\} + \frac{4}{3}N$$

$$Q = \left(1-\frac{K_b}{K_s}\right)K_s / \left(1-\frac{K_b}{K_s}+\frac{K_s}{K_f}\right)$$

$$R = {}^2K_s / \left(1-\frac{K_b}{K_s}+\frac{K_s}{K_f}\right)$$

where Ø is the porosity (fluid volume-fraction).

The density terms $\rho_{ij}$ are related to the density of the solid $\rho_s$ and fluid $\rho_f$ by $$\rho_{11}=(1-\emptyset)\rho_s+(\alpha-1)\emptyset\rho_f$$

$$\rho_{12}=-(\alpha-1)\emptyset\rho_f$$

$$\rho_{22}=\alpha\emptyset\rho_f$$

where α>1 is a purely geometrical quantity independent of solid or fluid densities.

The scalar displacement potentials of the fast and slow compressional waves are $\Pi_+, \Pi_-$, respectively. The vector potential of the shear wave is $\Psi$. The displacements for the fluid-saturated porous solid are then obtained from the potential function as $$u = v\,\Pi_+ + \nabla \Pi_- + \nabla \times \Psi$$

$$U = -G_+ \nabla \Pi_+ - G_- \nabla \Pi_- + (1-\alpha^{-1})\nabla \times \Psi$$

where $$G_\pm = (c_\pm^2 \rho_{11} - P)/(c_\pm^2 \rho_{12} - Q)$$

$$\Delta = P\rho_{22} + R\rho_{11} - 2Q\rho_{12}$$

The boundary conditions on the hole surface are continuity of normal stress disappearance of tangential stress, conservation of fluid volume between the discontinuity in pressure and the relative velocities in porous media where the open-pore boundary condition is assumed. FIG. 9 shows the x-axis 94, y-axis 98, and z-axis 96 used in the derivation and the configuration of the hole 92 having radius a 100 in the plate 90.

For harmonic waves, the average energy flux per unit area is defined by:

$$\sigma_m = (P - QG_+)k_+^{3/2}\exp(ik_+ r)A_m + (P - QG_-)k_-^{3/2}\exp(ik_- r)B_m$$

The scattering cross-section is defined by the ratio of the flux through the surface of radius r (exterior to the hole) to the incident average energy flux. This relationship yields:

$$\gamma = \frac{2}{(P - QG_+)k_+^3}\sum_{n=0}^{\infty}\frac{1}{\varepsilon_n}[U_n \bar{\sigma}_n^* + U_n^* \bar{\sigma}_r 2Nk_s^2 C_n C_n^*]$$

Other relationships, such as the velocity of the wave, involve a dependence on the elastic constants of the membrane. These relationships can also be useful in the characterization of defects, the structure, and the material characteristics of the membrane.

Using the solution to the potential equations and the definition of the scattering cross-section, the effective attenuation of an elastic wave due to the presence of a hole of a known size in a porous plate can be calculated and, in particular, the effect of the plate porosity on the scattered field from a hole can be determined. The calculations utilize approximate material properties for a porous polymeric material and specific material properties for polyvinylidene difluoride (PVDF), a material used in the formation of membranes. The skeletal modulus and density of the membrane are calculated from simple volume fraction arguments to be $K_s = 0.38$ GPα and $\rho_s = 1.76$ Mg/m$^3$. Water is assumed to fill the pores as well as the hole from which the wave is scattered, and be appropriately described by $K_f = 2.25$ GPα and $\rho_f = 1.00$ Mg/m$^3$. In addition, the overall porosity of the material is assumed to be forty percent, or $\emptyset = 0.40$. Initial calculations are made for $K_b = N = 0$. The modeling shows the effect of material properties on the amplitude of the scattered field and the significant reduction in the amplitude of the scattering cross-section that occurs when defects are detected in a porous fluid-filled plate.

Figure 10:
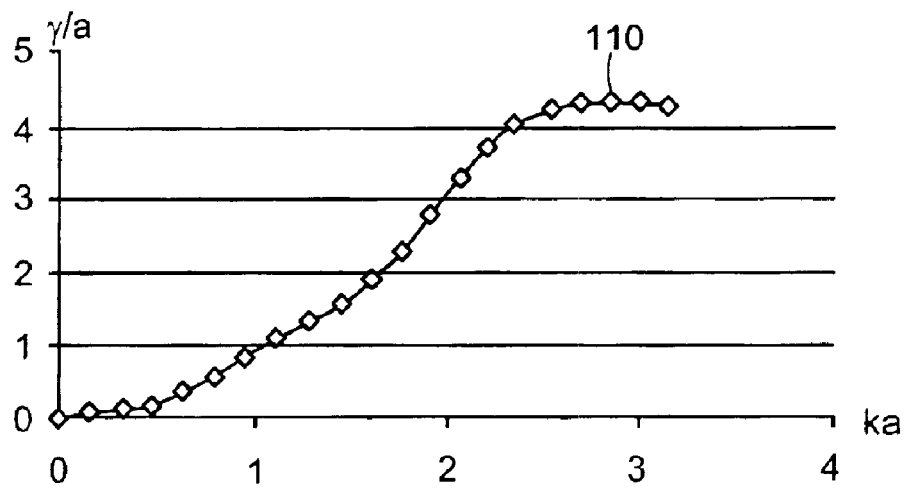
FIG. 10 illustrates the relationship between the scattering cross section of a hole in a plate, normalized by the radius of the hole, and a corresponding non-dimensional wave number.

Results from the modeling show the ability to detect defects within a porous membrane. Membranes having different porosities produce different scattering patterns, depending upon the diameter of the hole or the defect within the membrane. FIG. 10 illustrates the relationship 110 between the scattering cross-section of the void normalized by the radius of the hole (γ/a) versus a non-dimensional wave number, ka, where "a" is the radius of the hole and "k" is the wave number and k=2π/λ. As in the case of an elastic plate, for smaller holes, a monotonic increase in back-scattered amplitude occurs with an increase in frequency or an increase in hole size, corresponding to an increase in the ka parameter.

FIG. 10 also represents the effect of fluid filling and porosity on the scattering from a void in a porous plate by an elastic wave. The magnitude of the scattered field is reduced by more than a factor of four at ka=1 by the presence of porosity in the plate. This difference is much smaller for smaller diameter holes and also is eliminated once the hole becomes large relative to the wavelength. These results point to the difficulties that can be expected in the quantification of hole size via elastic waves if the porosity of the material is not well characterized. When a signal is obtained and the hole size is determined from the signal amplitude, a large hole in a material with high porosity would produce the same signal as a smaller hole in a plate with low porosity. Thus, determination of the membrane hole size requires knowledge of the four material moduli as well as the porosity.

Figure 11:
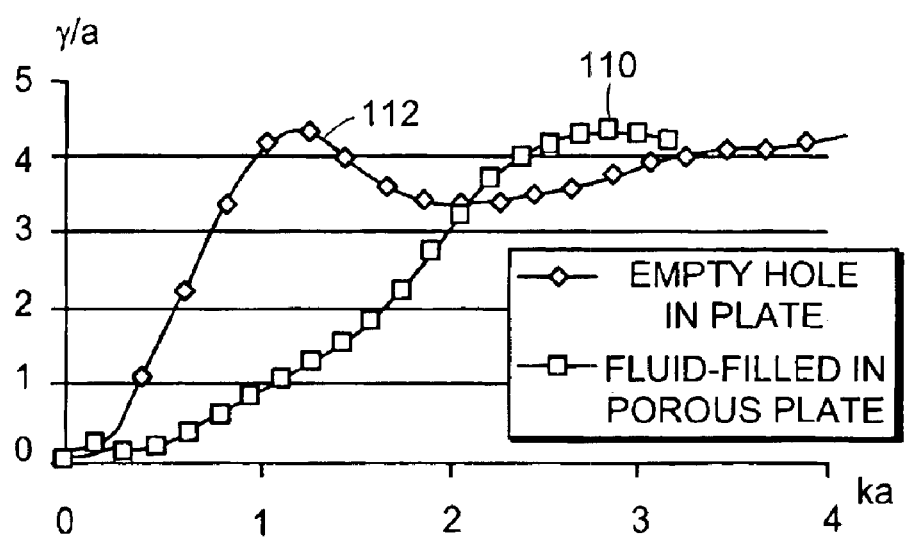
FIG. 11 illustrates a comparison between a curve showing the scattering cross-section of a fluid filled hole in a porous plate and a curve showing a scattering cross-section for an empty hole in a dense plate.

FIG. 11 shows a comparison between a first curve 110 showing the scattering cross-section for a void in a porous fluid filled PVDF membrane and a second curve 112 plotted for the scattered field from an empty hole in a fully dense, PVDF elastic plate. Curve 110 shows an attenuation of the signal in a porous plate compared to the signal in a solid plate, as displayed by curve 112. The differences between the scattering cross section for the porous membrane 110 and the dense elastic plate 112 is caused by the amount of porosity of the membrane and the presence of a dense fluid in the membrane. The difference between the signals as represented by the curves 110, 112 is also dependent upon the bulk modulus of the material forming the membranes and upon the type of fluid that fills the pores. For example, a signal produced in a membrane having gas filling the pores can be different from a signal produced in a membrane having fluid filling the pores.

Figure 12:
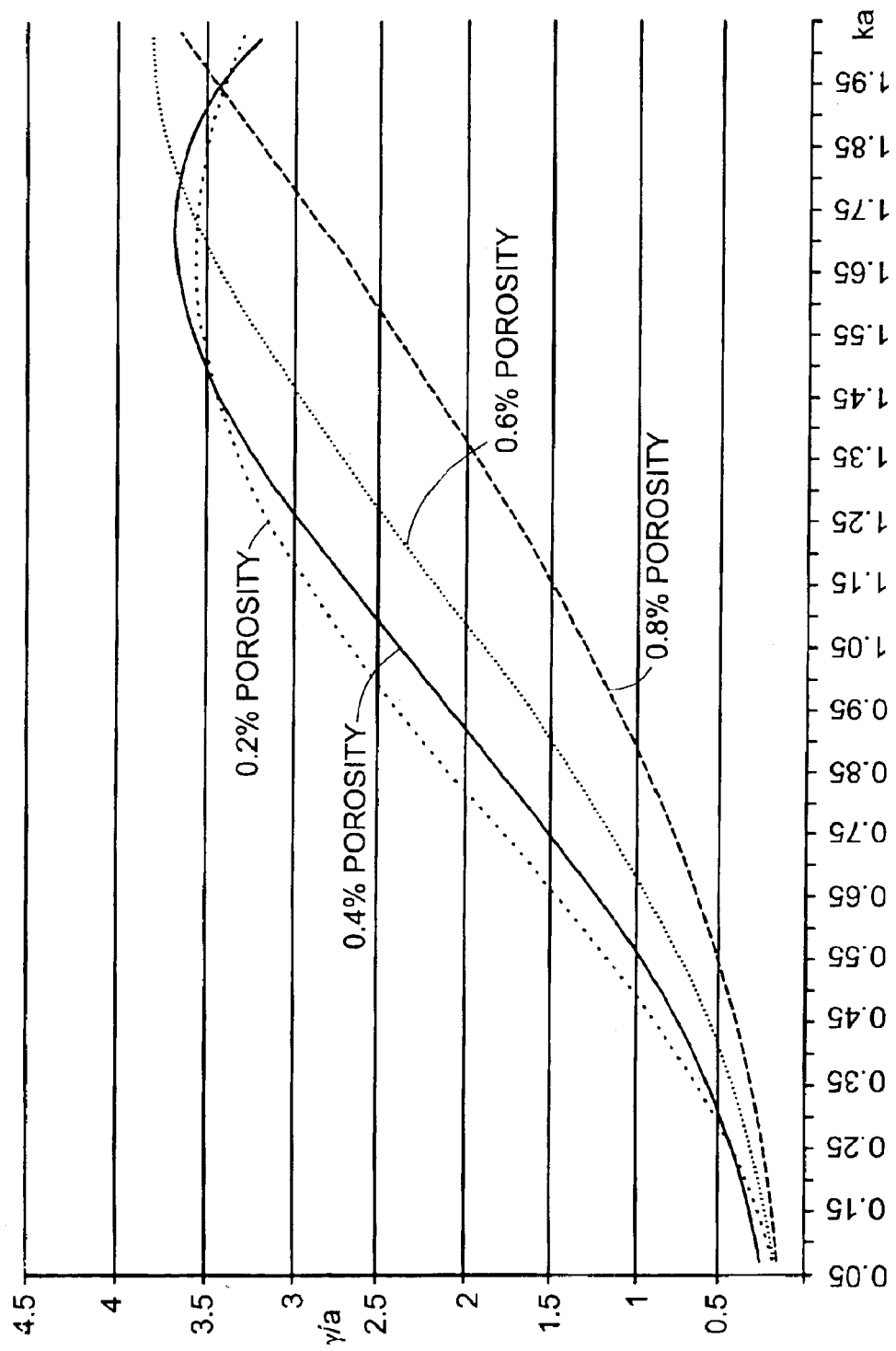
FIG. 12 illustrates the effect of porosity on a back scattered signal in a membrane.

The effect of the material properties and, in particular, the effect of various membrane porosities on the back-scattered signal is shown in FIG. 12. As the porosity of the membrane is increased, the slope of the curve representing the relationship between the normalized scattering cross section and the non-dimensional wave number, decreases. FIG. 12 also illustrates that the difference in porosity among different membranes should be taken into account in order to avoid either an overestimate or an underestimate of the defect size.

Figure 13:
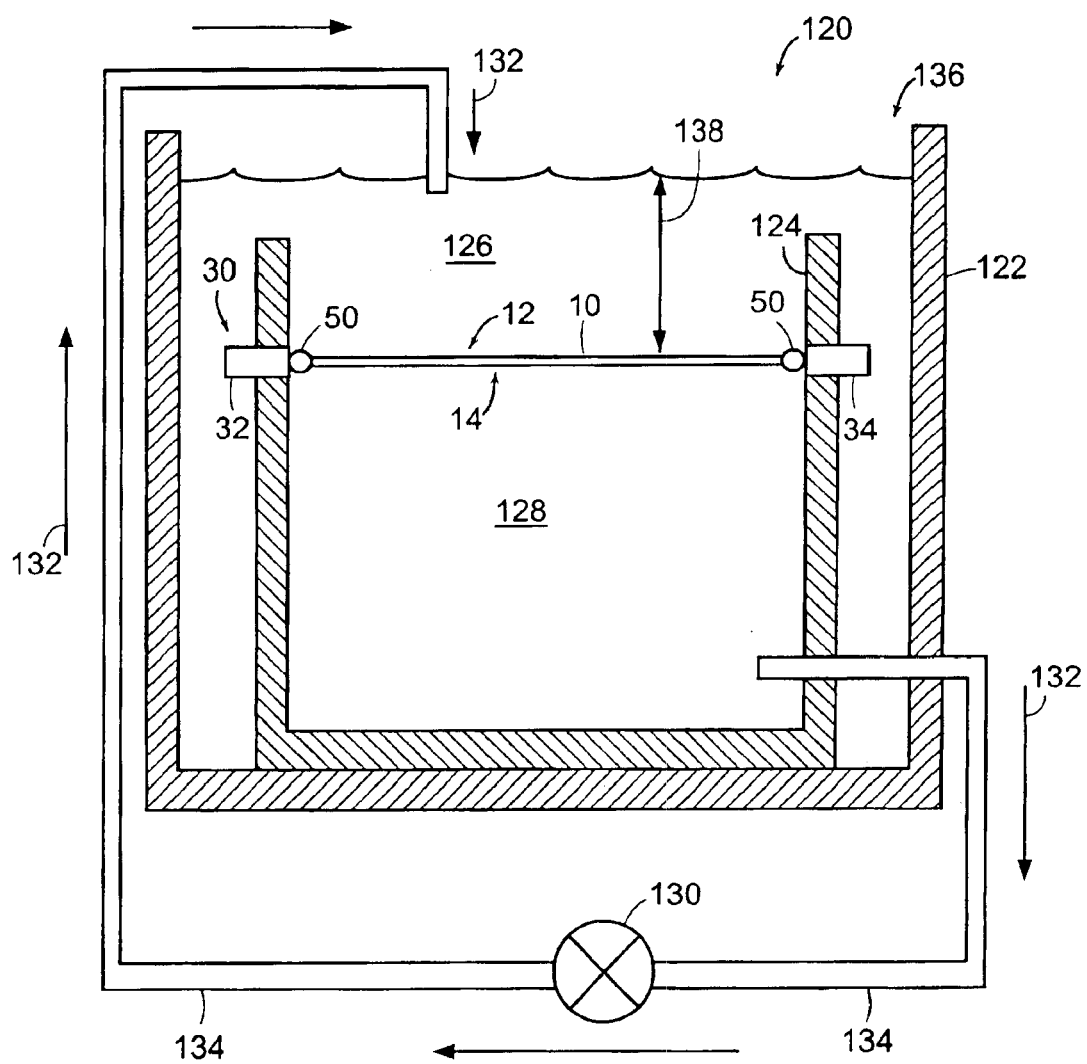
FIG. 13 illustrates a membrane testing system.

FIG. 13 illustrates a membrane testing system 120 including a permeation cell 136 and a pump 130. The permeation cell 136 includes a first chamber 122 and a second chamber 124 where the second chamber 124 is located within the first chamber 122. A membrane 10 is secured within the second chamber 124 and acts as a barrier between the first chamber 122 and the second chamber 124. The first boundary 12 of membrane 10 abuts a fluid medium 126 located within the first chamber 122. The second boundary 14 of the membrane 10 abuts a gaseous medium 128 or dry portion within the second chamber 124. The gaseous medium within the second chamber 124 is separated from the fluid medium 126 within the first chamber 122 by the membrane 10. This arrangement allows the fluid medium 126 to pass through the membrane 10 and into the dry portion 128 of the second chamber 124 during testing of the membrane.

Fluid that moves through the membrane 10 and into the gaseous medium 128 of the second chamber 124 is removed from the second chamber 124 by a pump 130. The pump 130 can be a peristaltic pump, for example. The pump 130 can be attached to a bottom portion of the second chamber 124 by a pump connector 134, such as a tube. Fluid from the second chamber 124 travels along path 132 through the pump connector 134. The fluid is carried from the second chamber 124 and is directed into the first chamber 122. Circulating the fluid within the permeation cell 136 maintains a moderate fluid depth 138 above the membrane 10. The fluid depth 138 can be several centimeters in depth.

The membrane 10 includes a coupling device 50 that allows a transducer 30 to be coupled to the membrane 10. As shown, the transducer 30 includes a transmitter 32 and a receiver 34. The testing frequency used in the system 120 is dependent upon the size of a defect in the membrane. The higher the testing frequency, the smaller the defect that is detectable by the system 120. For example, transducers 30 having an operating frequency of 90–100 MHz can be used to detect the presence of defects of less than five micrometers in size. Using transducers with an increased operating frequency allows the detection of relatively smaller defects within the membrane. The size of the defect that is detected in the membrane can be decreased by increasing the operating frequency.

The transducers 30 can be connected to a data acquisition device, such as a computer, in order to store the signals obtained from the membranes. The stored signals can then be compared electronically or visually to a reference signal to determine the membrane characteristics of the membrane, such as the presence of a defect in the membrane.

Figure 14:
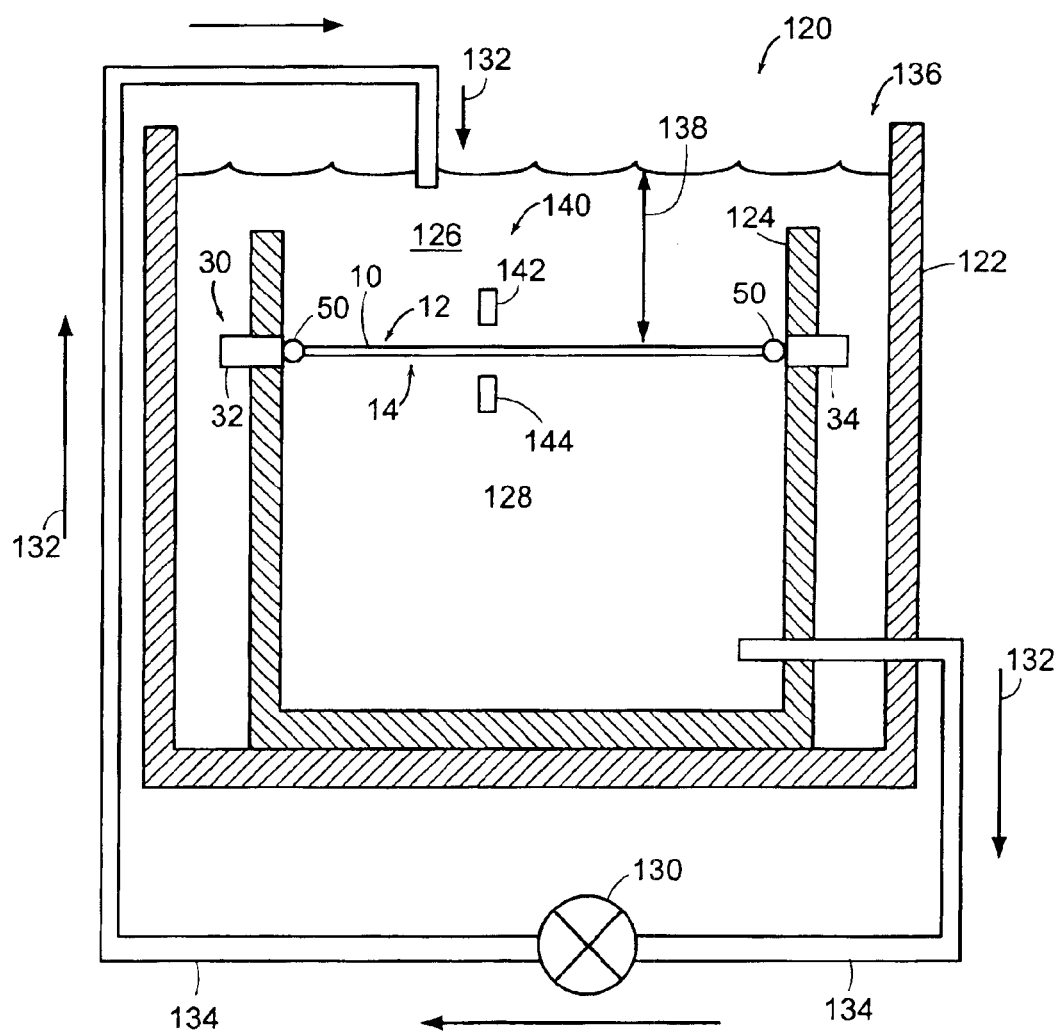
FIG. 14 illustrates an alternate configuration of a membrane testing system.

FIG. 13 illustrates transducers 30 located along a long axis of the membrane 10. The transducer 30 is used to determine the presence of defects within the membrane 10. FIG. 14 illustrates the use of a second sensor 140 mounted approximately normal to the surfaces 12, 14 of the membrane 10. The second sensor 140 can include both a transmitter 142 and a receiver 144. The second sensor 140 can be used to determine the porosity of the membrane 10 and can be used in conjunction with the transducer 30 as part of the membrane testing system 120. The second sensor 140 can be used to determine the pore size of the membrane 10.

Figure 15:
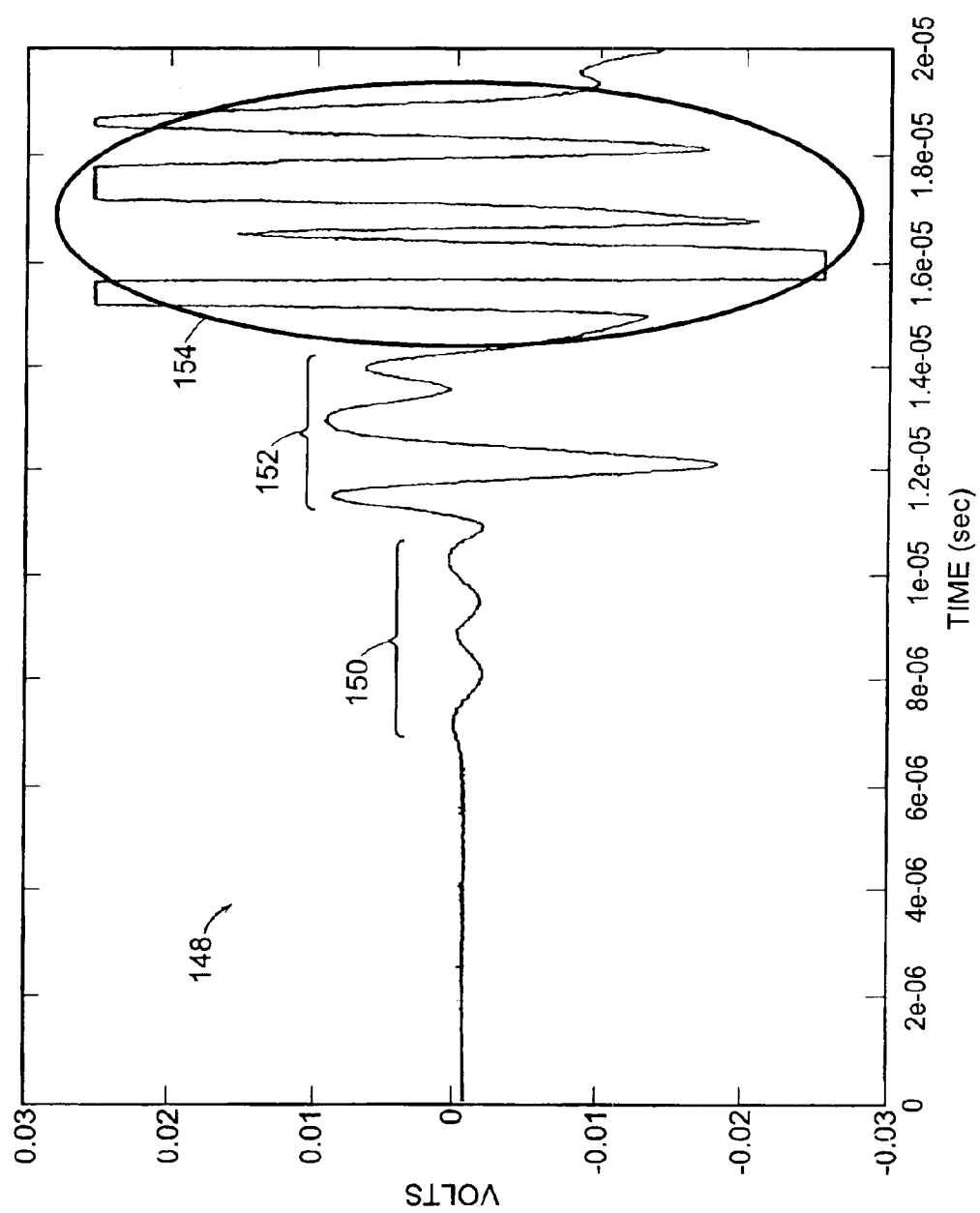
FIG. 15 illustrates a signal showing the presence of fast compression waves and slow compression waves in a membrane excited by a plate wave.

FIG. 15 illustrates a graph showing a signal or fingerprint of a membrane obtained by creating a plate wave in a membrane using an ultrasonic source. The signal 148 illustrates several phenomena, including the presence of fast compression waves 150 traveling through the membrane 10, slow compression waves 152 traveling through the membrane 10, and a portion of the signal representing the ultrasonic wave traveling through water 154. Fast compression waves 150 are sensitive to the total porosity of a membrane. Therefore, the fast compression waves 150 can be used to determine an unknown porosity of a membrane by comparing the fingerprint or signal 148 of the unknown membrane to the fingerprint or signal of a membrane having a known porosity. Slow compression waves 152 are less sensitive to membrane porosity and are used to indicate material characteristics of a membrane. For example, slow compression waves can be used to determine the presence of a defect in a membrane, and the type of material that forms a membrane. Slow compression waves can also be sensitive to the different types of polymer blends that form the membranes. Since the moduli are dependent upon material composition, the velocity of the slow compression waves can also tell the consistency of blends of polymers forming the membrane. Furthermore, membrane fouling caused by the use of the membrane as a filter can influence the slow compression waves. Note that the fast compression waves are also influenced by membrane fouling since the overall porosity of the membrane changes when it is fouled.

The formation of fast compression waves and slow compression waves in the membrane is caused by the superposition of plate waves within the fluid and solid portions of the membrane. Transmission of plate waves along the membrane leads to movement of fluid within the membrane's pores. The actual movement or "sloshing" of the fluid inside the pores of the membrane is responsible for the separation of the compression waves into fast compression waves and slow compression waves within the membrane. The fluid within the pores of the membrane can be a gas, such as air, or a liquid, such as water, for example.

Figure 16:
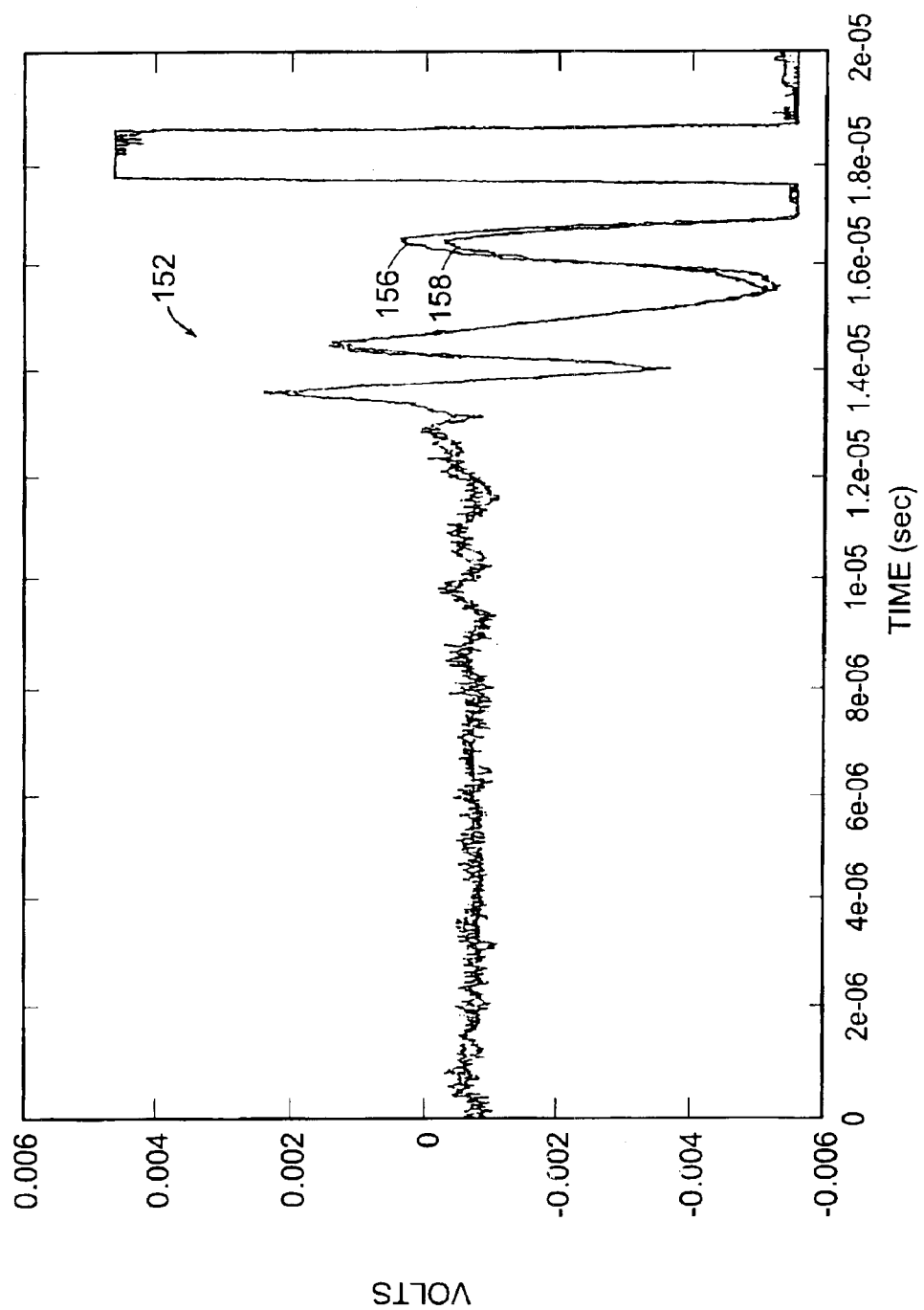
FIG. 16 shows a comparison of two signals produced in membranes.

FIG. 16 illustrates a comparison between two curves 156 and 158 representing the fingerprints for two different membranes and shows the applicability of slow compression waves in determining the presence of a defect within the membrane. The first curve 156 represents the signal for a membrane having a known porosity and no defects. An ultrasonic signal was delivered to the membrane at a frequency of one MHz. The second curve, curve 158, represents a signal for a membrane having the same porosity and same material composition of curve 156, and having a 0.7 mm void or defect within the membrane. Ultrasonic testing of the membrane was also performed at a frequency of one MHz.

In comparing the defect-free membrane with the membrane having a defect, a difference between curves 156 and 158 is present in the slow compression wave area 152 of the curves. The amplitude of what is either the trailing edge of the first compression wave or the slow compression waves for the membrane having the defect is less than the amplitude of the slow compression waves for the defect-free membrane. This comparison of the signals or fingerprints of a defect-free membrane with a defect-inclusive membrane shows the ability of elastic plate waves to indicate the presence of a defect within a membrane.

Figure 17:
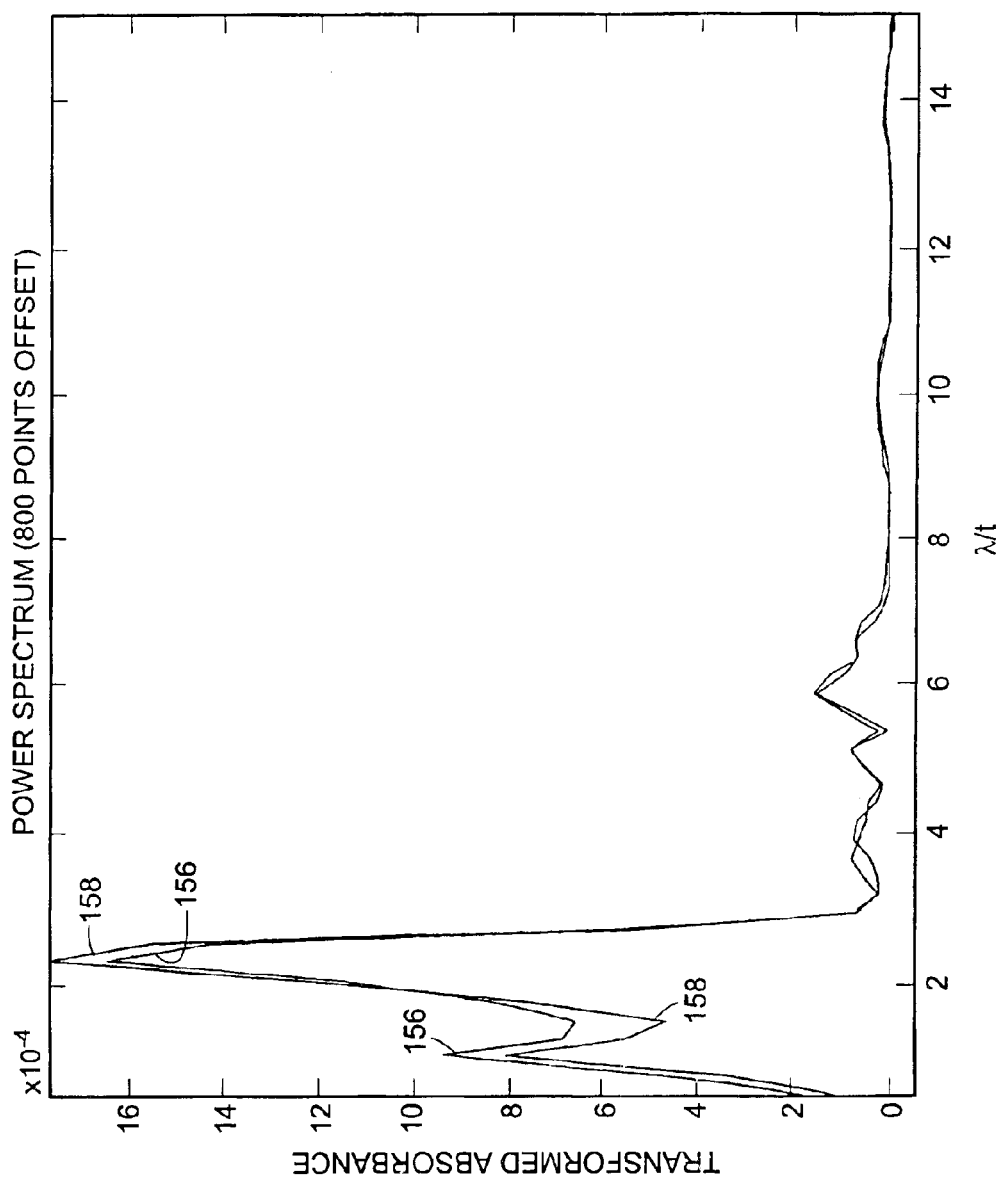
FIG. 17 shows a comparison of two Fourier transformed signals produced in membranes.

To more clearly show the difference in amplitude between curves 156 and 158, FIG. 17 illustrates a Fourier transform of the slow compression wave area 152. The compression wave from the defect-free membrane, as shown by curve 156, is shifted to the right of the wave measured in the defective membrane, as shown by curve 158, while the total area below both curves 156 and 158 remains the same. This indicates that the defect in the membrane slows the compression wave, but does not dissipate the energy of the wave.

The slow waves of FIG. 15 can also be used as a calibration guide to determine the integrity of a membrane after use. For example, during the process of drug filtration, the membrane integrity should be determined after filtration is completed to ensure that a defect has not been created in the membrane during the filtration process. Presence of a defect or an increase in the porosity of the membrane after the filtration process can indicate that the drug or solution was not properly filtered by the membrane. To determine the integrity of the membrane after the filtration process, the membrane is first cleaned to remove any proteins that have adhered to the membrane during the filtration process. A signal is then transmitted through the membrane and the slow wave traveling through the membrane is determined. A comparison of the slow wave after cleaning of the filter and with the slow wave from a reference membrane or from the membrane prior to filtration of the drug can indicate the presence of a defect in the membrane.

The slow wave can also be used to determine whether a filter has been cleaned adequately such that the filter can be used in subsequent filtering processes. In certain applications membranes can be reused. However, in order to be reused, the membranes should be adequately cleaned to prevent cross contamination between one batch of solution to be filtered with another batch.

While the slow wave can be used on its own to determine the integrity of the filter, depending on the material that forms the membrane, both the slow wave 150 and the fast wave 152 can be used to determine the integrity of the membrane. For example, comparison of the ratio of amplitudes between the slow wave 150 and the fast wave 152 can be used to determine the cleanliness of a membrane. The ratio of amplitudes can be determined using several different methods. For example, the signal processing can be used to determine when the peak energy from the slow wave arrives and when the peak energy of the fast wave arrives in the membrane. Cross correlation of these peak energies can be employed to determine the integrity of the filter or the cleanliness of the filter. This process is based upon using the relatively high sampling rate of the signal in the membrane. In another method, the phase difference between the slow wave 150 and the fast wave 152 can be determined using Fourier transforms. A phase shift indicates the presence of a defect in the membrane. Time measurements can also be used to determine the integrity of the filter. That is, the occurrences when the energy peaks hit the membrane at different times can indicate the integrity of the membrane. Note that in addition to providing information about defects in the membrane, the time difference between the peaks of the slow and fast compression waves can provide information about membrane fouling.

Figure 18:
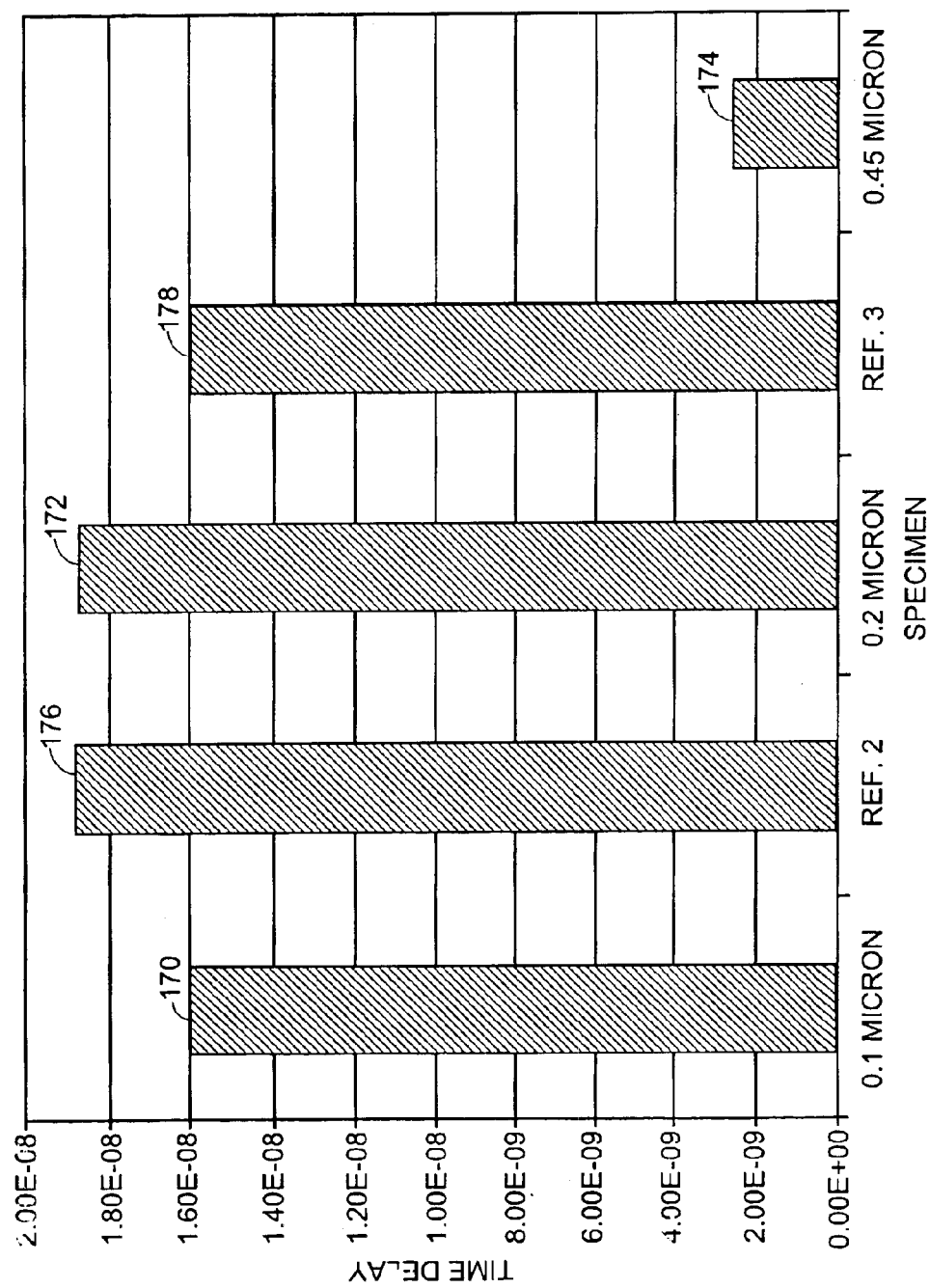
FIG. 18 illustrates the time delay of a fast compression wave.

FIG. 18 illustrates a comparison of the time delay of fast compression waves in membranes having varying pore sizes. As stated above, fast compression waves are sensitive to the total porosity of a membrane. To determine the effect of pore size on the fast compression waves, three different membranes having the same porosities but different pore sizes were tested. Membranes having a 0.1 micrometer pore size, a 0.2 micrometer pore size and a 0.45 micrometer pore size were tested by propagating an acoustic wave through the membranes and evaluating the resulting signal. The membranes having the 0.1 micrometer and 0.2 micrometer pore sizes were formed of the same polymer blend while the membrane having the 0.45 micrometer pore size was formed of a different polymer blend than the 0.1 micrometer and 0.2 micrometer pore sized membranes.

FIG. 18 illustrates the time delay of the fast compression wave in the membranes having a 0.1 micrometer pore size 170, a 0.2 micrometer pore size 172, and a 0.45 micrometer pore size 174. The time delay of the fast compression wave for two reference samples 176, 178 was also determined. FIG. 18 shows little difference in the time delay of the fast compression wave between the membrane having the 0.1 micrometer pore size and the membrane having the 0.2 micrometer pore size. There was a difference between these two membranes and the membrane having the 0.45 micrometer pore size. The difference, however, is because the membrane having the 4.5 micrometer pore size is made from a different polymer blend than either the membrane having the 0.1 micrometer pore size or the membrane having the 0.2 micrometer pore size. The graph shows that fast compression waves are sensitive to the type of polymer blend that forms a membrane but are not sensitive to pore size. Generally, the moduli of a membrane affects the time delay of fast compression waves within the membranes.

The process of using time delay of fast compression waves to distinguish membrane materials can be applied in the determination of the type of materials that forms a membrane having an unknown composition. For example, in the case where a membrane is unidentified by a marking or a label, measurement of the time delay of the fast compression waves in the membrane can provide information to characterize the material forming the membrane. Such an application can also be used in quality control during manufacture of a filter having a membrane. For example, membranes are formed from a blend of materials. Prior to incorporating the membranes as part of a filtering device, the variability of the materials that form the membrane is unknown. Measuring the time delay of the fast compression waves in the membranes can be done before the membranes are incorporated into the filter device to determine the variability of the materials forming the membrane. If the variability is determined to be too great in a quality review process, the membranes can be discarded prior to incorporation within a filtering device. Such an application allows for quality control during the manufacturing process.

While the measurements shown have assumed a linear response, a non-linear response of the membranes to the signals can also be used to determine characteristics of the membrane. For example, if a signal having a 10 MHz frequency is delivered into the membrane and a signal having a frequency of 10.1 MHz is received from the membrane, such a signal is non-linear. This non-linear response can be used to determine characteristics of the membrane, such as membrane fouling. The non-linear response can be produced in a membrane when the membrane is either wet or dry.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for determining a porous film characteristic comprising the steps of:
 a) acoustically coupling at least one transducer to a porous film;
 b) producing a plate wave in the porous film by propagating an acoustic wave within the porous film;
 c) obtaining a representative signal for the porous film, distinguishing a fast compression wave and a slow compression wave in the porous film;
 d) determining the porous film characteristic from the representative signal.

2. The method of claim 1 further comprising acoustically coupling the at least one transducer to the porous film at an angle relative to the surface of the porous film.

3. The method of claim 1 further comprising acoustically coupling the at least one transducer to the porous film along an axis parallel to the surface of the porous film.

4. The method of claim 1 further comprising impedance matching the at least one transducer to the porous film material.

5. The method of claim 4 further comprising attaching an epoxy resin coupling device having a glass particle filler between the at least one transducer and the porous film.

6. The method of claim 1 wherein the step of determining the characteristic of the porous film comprises determining the material properties of the porous film.

7. The method of claim 1 wherein the step of determining the characteristic of the porous film comprises determining the total porosity of the porous film.

8. The method of claim 1 wherein the step of determining the characteristic of the porous film comprises determining the presence of a defect in the porous film.

9. The method of claim 8 wherein the defect is less than about one wavelength in size.

10. The method of claim 1 further comprising determining the time difference between the fast compression wave and the slow compression wave.

11. The method of claim 10 wherein the step of determining the characteristic of the porous film comprises determining the total porosity of the porous film.

12. The method of claim 10 wherein the step of determining the characteristic of the porous film comprises determining the presence of a defect in the porous film.

13. The method of claim 1 wherein at least one surface of the porous film contacts a liquid medium.

14. The method of claim 1 wherein at least one surface of the porous film contacts a gaseous medium.

15. The method of claim 1 further comprising coupling a second transducer normal to a surface of the porous film.

16. The method of claim 15 further comprising determining the porosity of the porous film.

17. The method of claim 15 further comprising determining the pore size of the porous film.

18. The method of claim 1 further comprising comparing the representative signal for the porous film with a reference signal from a reference porous film.

19. The method of claim 1 wherein the porous film is a membrane.

20. The method of claim 1, wherein the step of obtaining a representative signal for the porous film includes distinguishing a slow compression wave in the porous film and the step of determining the porous film characteristic from the representative signal includes analyzing the slow compression wave.

21. The method of claim 1, wherein the step of obtaining a representative signal for the porous film includes distinguishing a fast compression wave in the porous film and the step of determining the porous film characteristic from the representative signal includes analyzing the fast compression wave.

22. A method for determining a material characteristic of a porous film comprising the steps of:

a) acoustically coupling at least one transducer to a porous film;

b) producing a plate wave in the porous film by propagating a sound wave within the porous film;

c) distinguishing a slow compression wave in the porous film; and d) analyzing the slow compression wave to determine the material characteristic of the porous film.

23. A method for determining the total porosity in a porous film comprising the steps of:

a) acoustically coupling at least one transducer to a porous film;

b) producing a plate wave in the porous film by propagating a sound wave within the porous film;

c) distinguishing a fast compression wave in the porous film; and d) analyzing the fast compression wave to determine the total porosity of the porous film.

24. The method of claim 1, wherein the plate wave is a Leaky Lamb wave.

25. The method of claim 22, wherein the plate wave is a Leaky Lamb wave.

26. The method of claim 23, wherein the plate wave is a Leaky Lamb wave.

27. The method of claim 1, wherein a free boundary surface of the film is about 10 wavelengths or less of an elastic disturbance.

28. The method of claim 22, wherein a free boundary surface of the film is about 10 wavelengths or less of an elastic disturbance.

29. The method of claim 23, wherein a free boundary surface of the film is about 10 wavelengths or less of an elastic disturbance.

* * * * *